(12) United States Patent
Hunter et al.

(10) Patent No.: US 7,933,435 B2
(45) Date of Patent: Apr. 26, 2011

(54) SYSTEM, METHOD, AND KIT FOR PROCESSING A MAGNIFIED IMAGE OF BIOLOGICAL MATERIAL TO IDENTIFY COMPONENTS OF A BIOLOGICAL OBJECT

(75) Inventors: Edward Hunter, San Diego, CA (US); Patrick M. Mc Donough, San Diego, CA (US); Ivana Mikic, San Diego, CA (US); Jeffrey H. Price, San Diego, CA (US)

(73) Assignee: VALA Sciences, Inc., LaJolla, CA (US)

( * ) Notice: Subject to any disclaimer, the term of this patent is extended or adjusted under 35 U.S.C. 154(b) by 1006 days.

(21) Appl. No.: 11/285,691

(22) Filed: Nov. 21, 2005

(65) Prior Publication Data

US 2008/0144895 A1 Jun. 19, 2008

(51) Int. Cl.
*G06K 9/00* (2006.01)
(52) U.S. Cl. .................................. 382/128; 382/134
(58) Field of Classification Search ........... 382/128–134
See application file for complete search history.

(56) References Cited

U.S. PATENT DOCUMENTS

| | | | | |
|---|---|---|---|---|
| 5,257,182 | A * | 10/1993 | Luck et al. | 382/224 |
| 5,548,661 | A | 8/1996 | Price et al. | 382/133 |
| 5,790,692 | A | 8/1998 | Price et al. | 382/133 |
| 5,790,710 | A | 8/1998 | Price et al. | 382/133 |
| 5,856,665 | A | 1/1999 | Price et al. | 250/205 |
| 5,932,872 | A | 8/1999 | Price | 250/201.3 |
| 5,989,835 | A | 11/1999 | Dunlay et al. | 435/7.2 |
| 5,995,143 | A | 11/1999 | Price et al. | 348/345 |
| 6,620,591 | B1 | 9/2003 | Dunlay et al. | 435/7.2 |
| 6,640,014 | B1 | 10/2003 | Price et al. | 382/255 |
| 6,741,755 | B1 * | 5/2004 | Blake et al. | 382/284 |
| 6,839,469 | B2 | 1/2005 | Nguyen et al. | 382/255 |
| 6,886,168 | B2 | 4/2005 | Callaway et al. | 719/316 |
| 6,956,961 | B2 | 10/2005 | Cong et al. | 382/133 |
| 2005/0002552 | A1 | 1/2005 | Dunn et al. | 382/133 |
| 2005/0009032 | A1 * | 1/2005 | Coleman et al. | 435/6 |
| 2007/0016373 | A1 | 1/2007 | Hunter et al. | 702/19 |

FOREIGN PATENT DOCUMENTS

| | | |
|---|---|---|
| WO | WO 02/067195 | 8/2002 |
| WO | WO 03/078965 | 9/2003 |
| WO | WO 2004/099773 | 11/2004 |
| WO | WO 2007/061971 | 5/2007 |

OTHER PUBLICATIONS

H. Ogawa, et al., (1995) *Proc. Natl. Acad. Sci. USA*, vol. 92, 11899-11903, Cell Biology.
International Search Report and Written Opinion for PCT/US2006/044936 (published as WO 2007/061971), mailed Aug. 10, 2007.

* cited by examiner

*Primary Examiner* — Anand Bhatnagar
*Assistant Examiner* — Alex Liew
(74) *Attorney, Agent, or Firm* — Terrance A. Meador; INCAPLAW

(57) ABSTRACT

A system, method and kit for processing an original image of biological material to identify certain components of a biological object by locating the biological object in the image, enhancing the image by sharpening components of interest in the object, and applying a contour-finding function to the enhanced image to create a contour mask. The contour mask may be processed to yield a segmented image divided by structural units of the biological material.

4 Claims, 17 Drawing Sheets

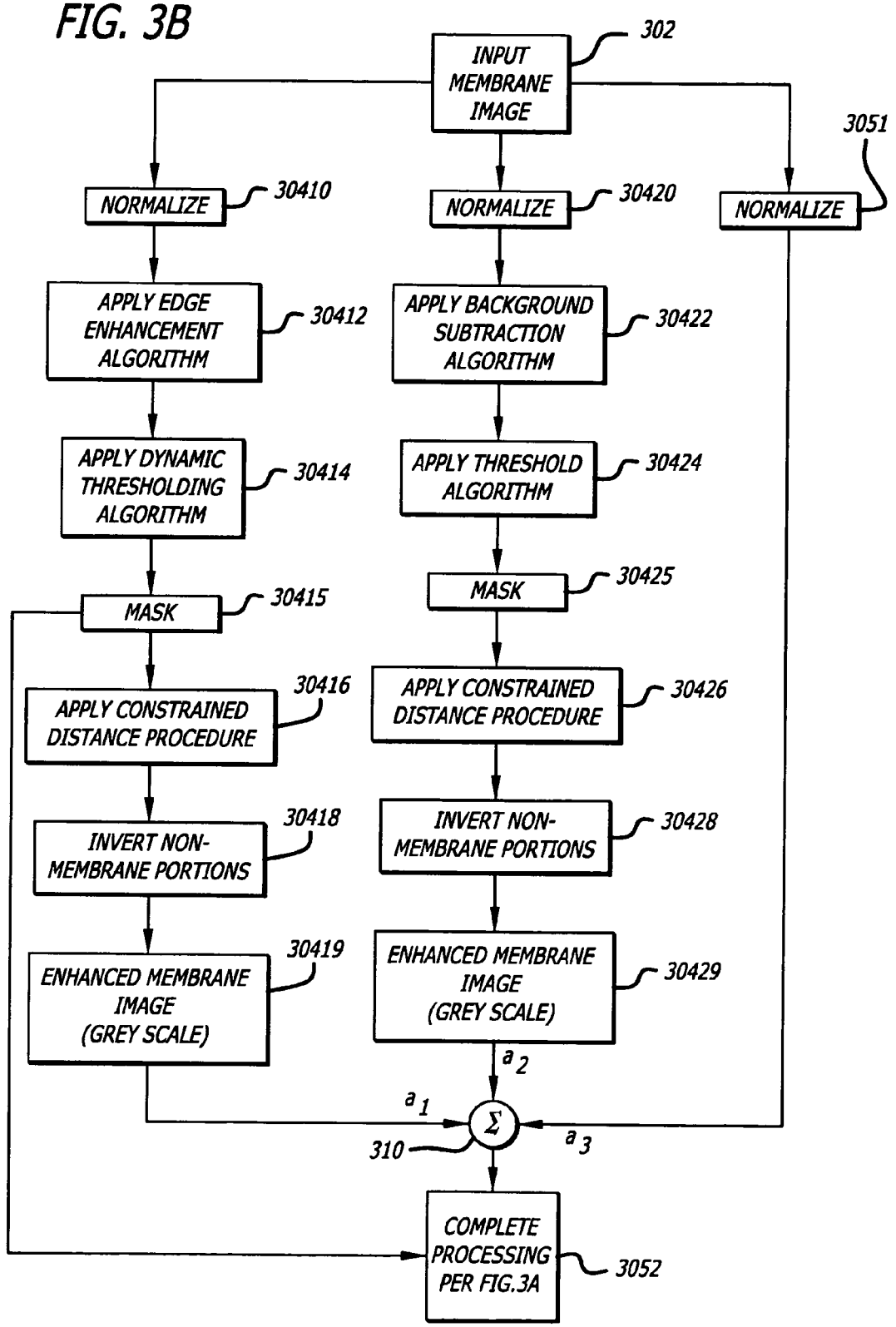

FIG. 4A
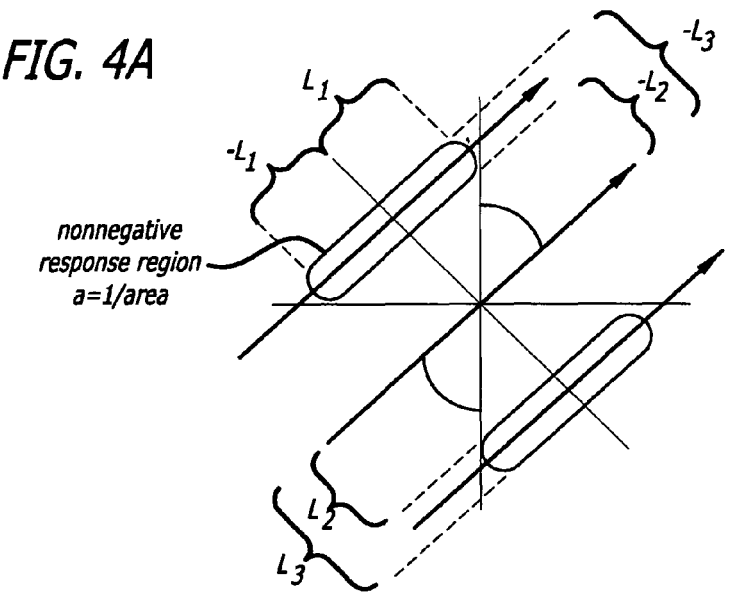
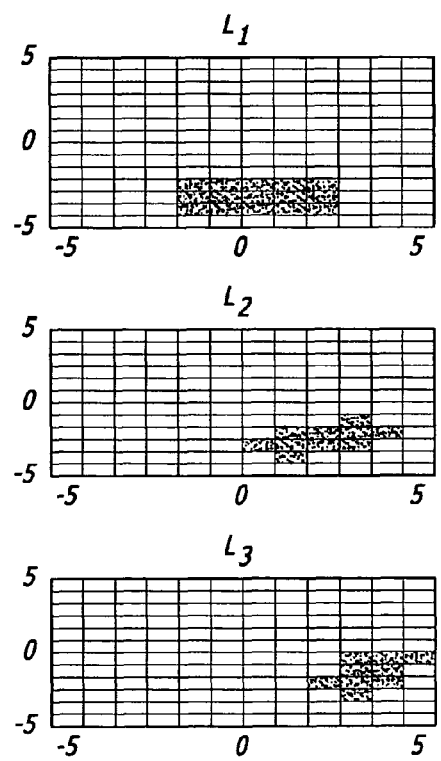
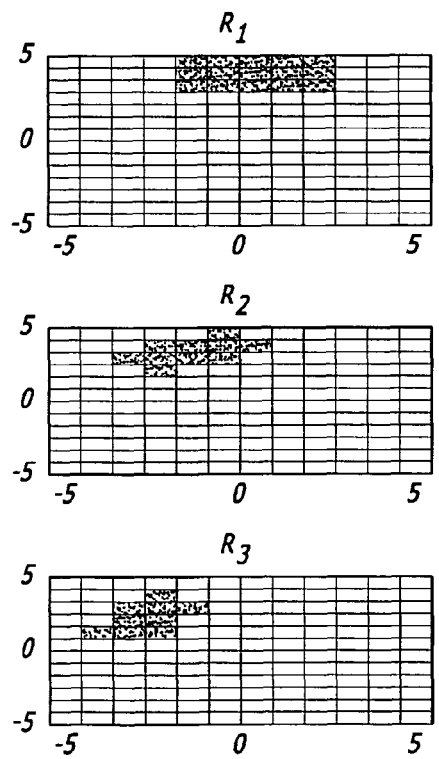
FIG. 4B

  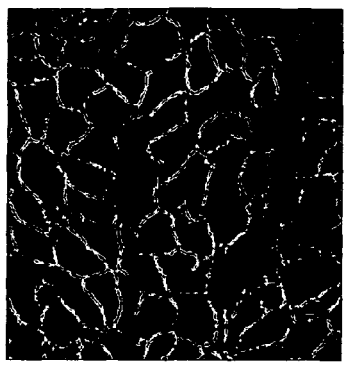
FIG. 5A  FIG. 5B  FIG. 5C
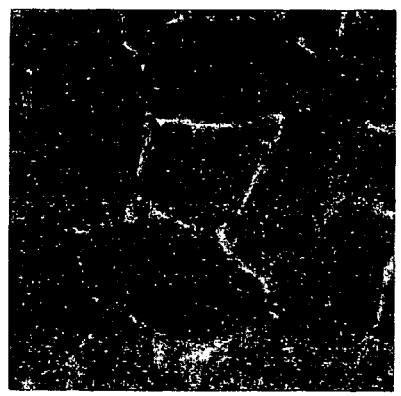
FIG. 6A: Membrane Channel
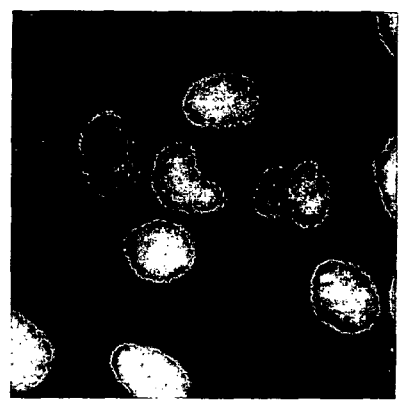
FIG. 6B: Nuclear Channel

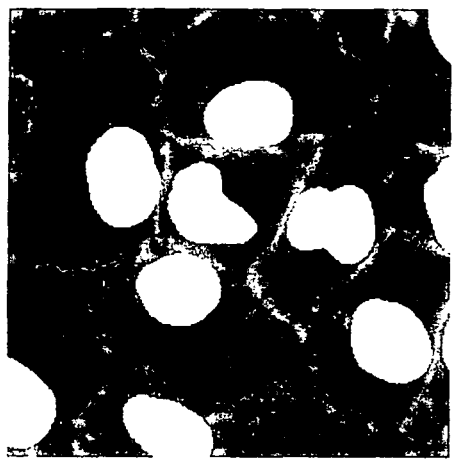
FIG: 6C: Nuclear Mask and Membrane Channel
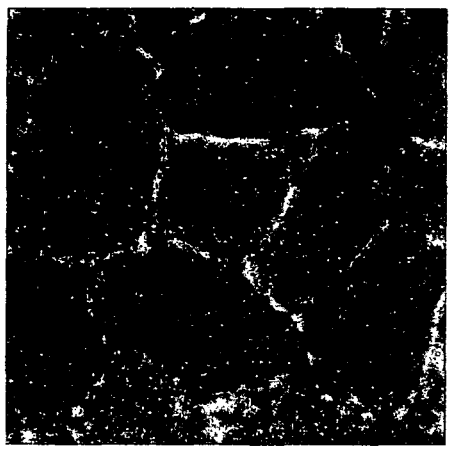
FIG. 6D: Normalized Image
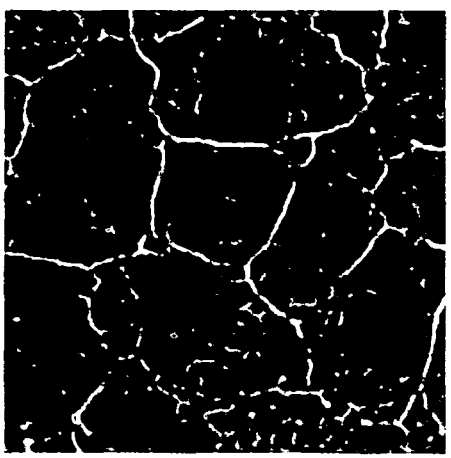
FIG. 6E: Filterbank Output

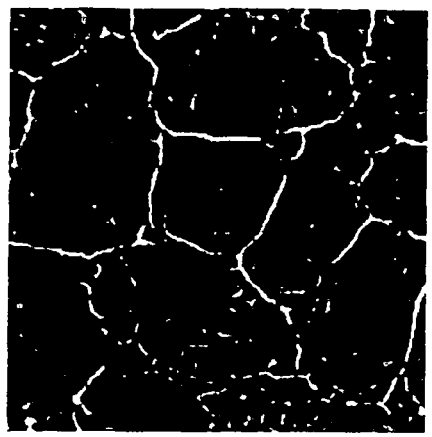
FIG. 6F: Membrane Segments and Filterbank Output
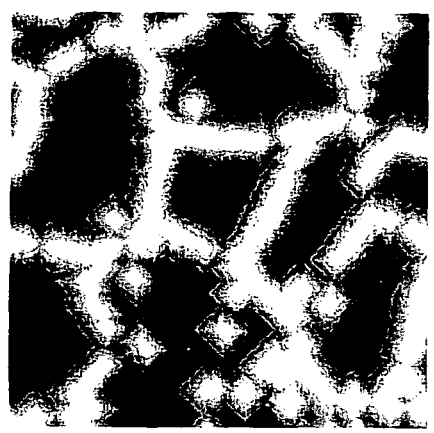
FIG. 6G: Membrane Segments and Inverse Distance From Membrane Segments
FIG. 6H: Final Membrane Enhanced Image

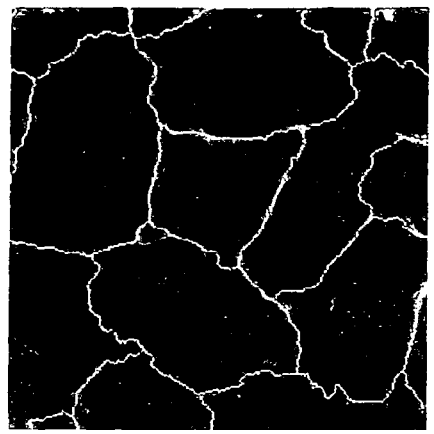
FIG. 6I: Nuclear Mask (Markers - Blue), Watershed Lines (Yellow) and Final Membrane Enhanced image
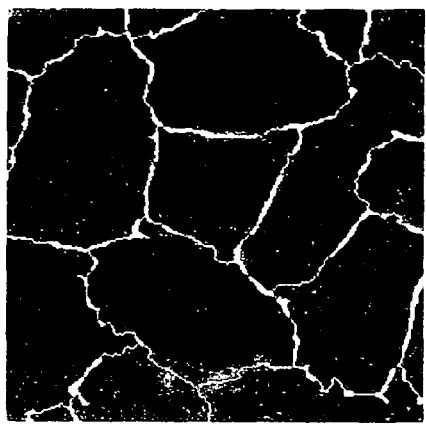
FIG. 6J: Final Membrane Mask

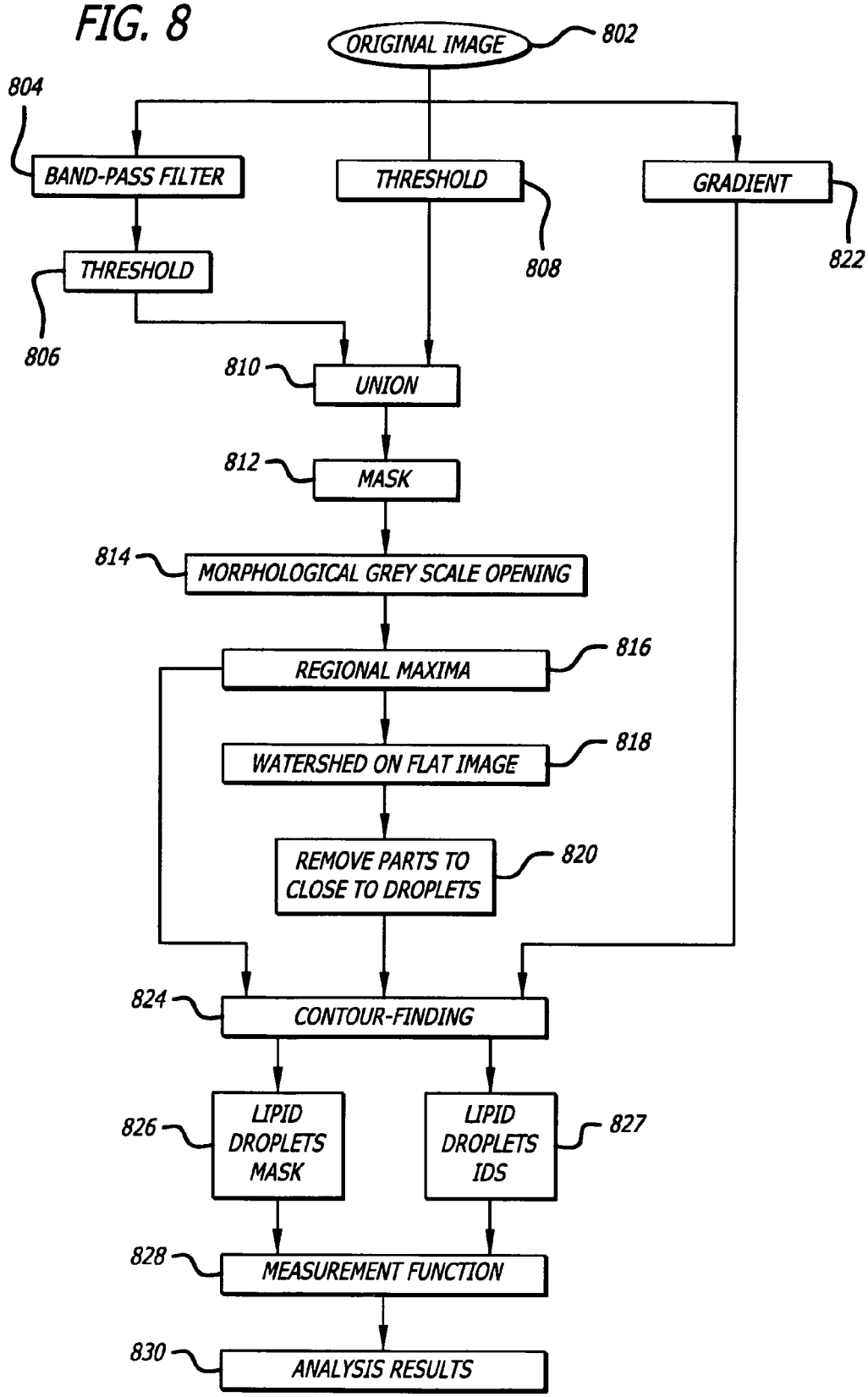

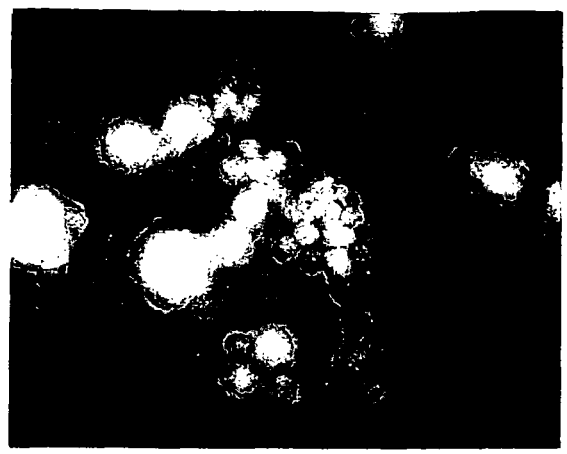
FIG. 9A: Original Image
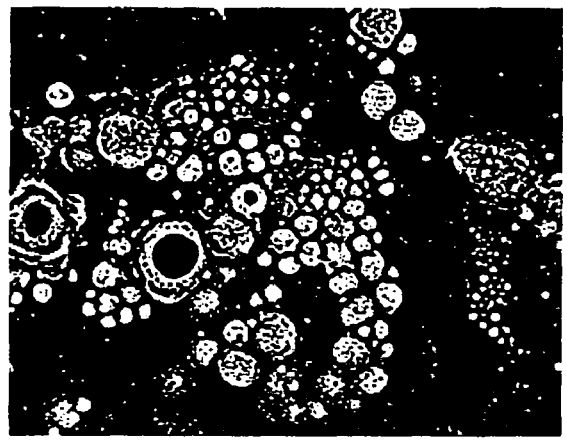
FIG. 9B: Filtered Image
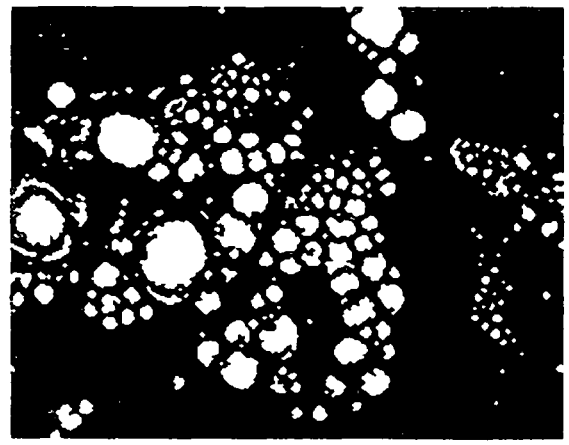
FIG. 9C: First Mask

FIG. 9D: Second Mask
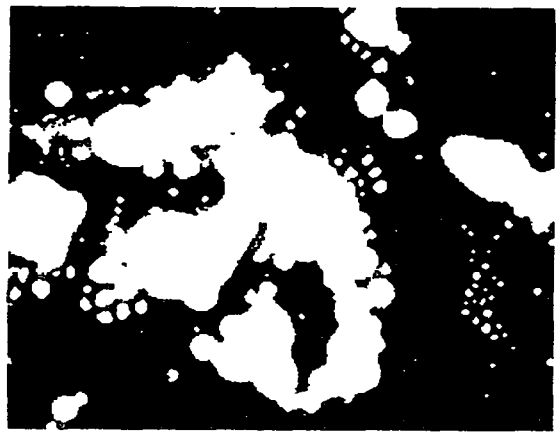
FIG. 9E: Combined Masks
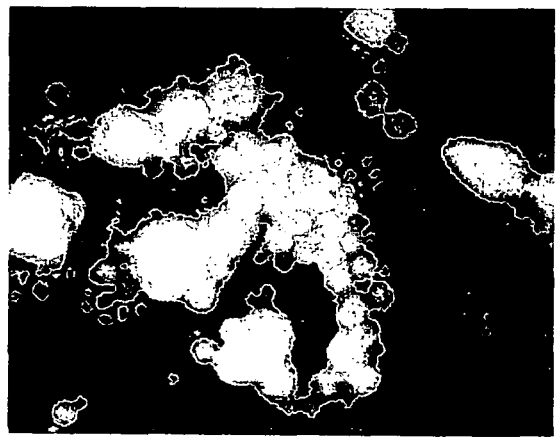
FIG. 9F: Masked Image

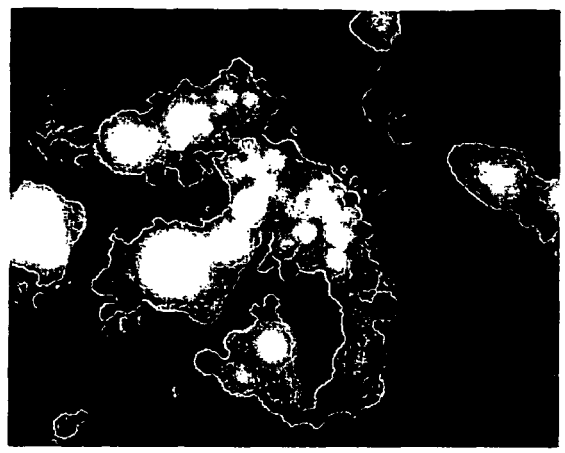
FIG. 9G: Cleaned Up (Regional Maxima Removed)
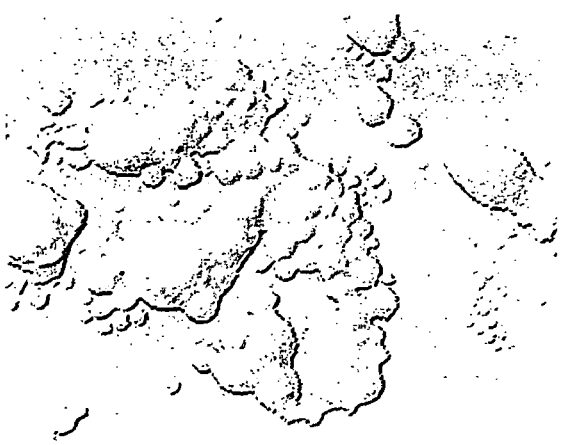
FIG. 9H: Droplet Markers
FIG. 9I: Background Marker

FIG. 9J: Gradient Image
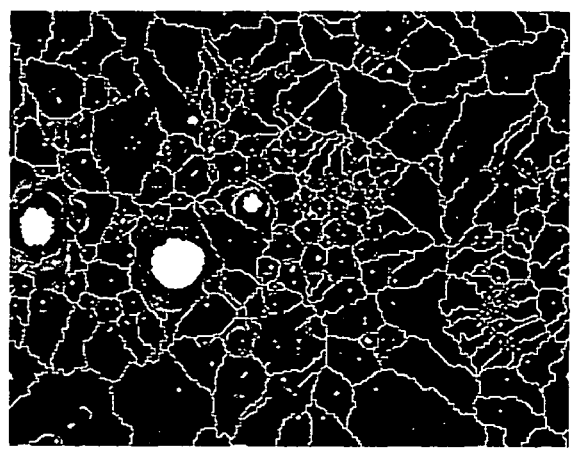
FIG. 9K: Gradient Image and Markers
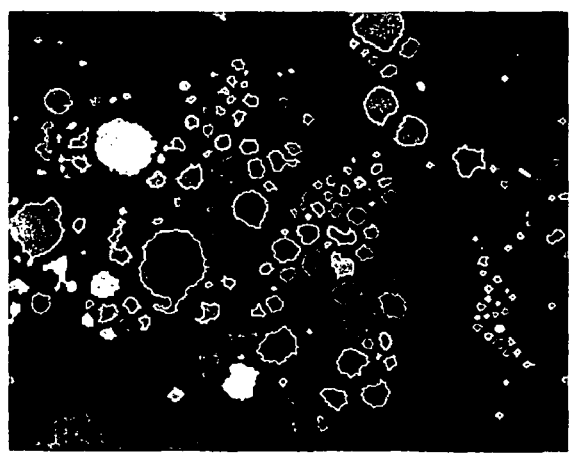
FIG. 9L: Final Result

SYSTEM, METHOD, AND KIT FOR PROCESSING A MAGNIFIED IMAGE OF BIOLOGICAL MATERIAL TO IDENTIFY COMPONENTS OF A BIOLOGICAL OBJECT

BACKGROUND OF THE INVENTION

The technical field concerns image processing. More particularly, the technical field covers processing a magnified image of biological material to identify one or more components of an object in the image. In addition, the technical field includes a combination of reagents to enhance the visualization of one or more components of an object in a magnified image of stimulated biological material and an automated process adapted to identify the components.

Biological material may include cells disposed in or on plastic or glass culture dishes, cells disposed on plastic or glass slides, and/or tissue sections mounted to plastic or glass slides.

Measurements of object features in magnified images of biological material are of increasing importance in the analysis of biological processes in automated high throughput screening (HTS) and in high content screening (HCS). For example, in HTS procedures developed for assaying cellular activity, each well of a two dimensional array of wells (in industry-standard multi-well dishes, slides, or chamber slides), contains cells that are exposed to a stimulus for some period of time (a "reaction period") during which the cells respond to the stimulus. Images are then generated from the cells in each well, by photomicroscopy and information respecting the response is obtained from the images and analyzed to evaluate the response.

In support of extracting information from cells, stain is applied to the cells to make certain features visually more distinct than others. A stain seeks and colors a particular element or material in the cells (stains are also called dyes). Following the reaction period, information about the cells' response to the stimulus may be evident by detecting shapes, locations, dimensions and quantities of stained material in the stimulated cells. Stain may be applied before and/or after stimulation by means of materials that may include, without limitation, chemical stains and/or antibodies. More than one stain may be applied, each to enhance visibility of a particular cellular feature. For example, an antibody fused with a fluorescent molecule may be transported into cytoplasm and bound to a specific enzyme presumed to be responsive to an applied stimulus. The stain enhances the visibility of that enzyme when the cellular material is subjected to an illumination that causes the molecule to fluoresce. Another stain having an affinity for cell nuclei may be applied to make cell nuclei visible at a certain illumination wavelength. Magnified images of the cells are obtained through a microscope and captured by a camera mounted to the microscope. The microscope is operated either automatically or manually to scan the array of wells and the camera takes one or more images of the stimulated, stained cells in each well. The images are passed to an automated image process that derives information from the images, based on the locations of the stained enzyme and nuclei. The information is processed to obtain parameter values that may be combined by a function to provide one or more measurements of the reaction.

Therefore, a step of staining biological material includes applying one or more reagents to the biological material that enhance visibility of components of the material when the stained material is illuminated at certain wavelengths or wavebands. Each stain is designed to be absorbed by a particular component of interest in order to enhance the visibility of that component when the stained material is illuminated. Staining helps an automated image process to "see" and distinguish these different structures in order to accurately measure one or more responses of the visualized biological material Images of the stained cells may be obtained while the cells are live, or after the cells have been chemically preserved with formaldehyde, methanol or other fixatives. In this regard, a step of fixing activated biological material includes applying one or more reagents to the material to stop the stimulated activity and lock the structure of the activated material against further change.

A measurement made by an automated image process requires that an image be reliably presented in a form that is manifest to the process. The image process does not perceive an image in the same way a human does. Instead, it discerns the image as an N×M array of picture elements ("pixels"), each constituted of a numerical representation of light intensity. An image includes one or more objects and may or may not include a background containing pixels of a certain intensity that contrasts with the intensity or intensities of the object pixels. An image composed of pixels defined on an array is referred to as a digital image or a digital picture. A digital image may be presented to a viewer on the screen of a display device such as a cathode ray tube (CRT), a flat panel display, a camera, or other equivalent device.

One difficult problem in the visualization of cell structures by automated image processes arises when the structures touch or overlap. For example, the analysis of cell membrane structure following activation of protein kinase C alpha (PKCα) requires that an automated image process be able to identify and distinguish the membranes whereto the PKCα migrates when stimulated in order to distinguish one cell from another. However, in cases where the cellular material is densely packed and/or agglomerated, an automated image process may have difficulty distinguishing cells whose membranes overlap and/or touch. The process may interpret a membrane boundary shared by adjacent cells as the membrane of one cell but may fail to identify an abutting cell sharing the membrane boundary. As a result, cells in an image may not be identified by the automated image process. The failure of the process to identify and/or count multiple cells with abutting boundaries may lead to deficiencies and inaccuracies in measurement of the activity of interest.

A further problem arises from the different cellular components that might be imaged for different responses or in cells with different structures. In this regard, membranes and nuclei are typically features of interest in responses that activate the membranes of many cells. A number of different proteins and other molecules may be stimulated to change location from the interior of a cell to its membrane. Among these are, for example, PKCs. Other substances may be stimulated to leave the cell membrane. Among these substances are, for example, cadherins. In other instances, substances may be stimulated to exchange locations at the membrane with other substances. A response causing transposition of substances to and/or from the membrane of a cell may be classed as a "membrane activation" response. Information about the cell's response may be obtained from an image of the membrane. When the transposing substances are stained, the cell membrane changes in visibility as transposition progresses. The outline of a cell's membrane is a closed trace that has no regular shape. Sometimes, the closed, irregularly shaped trace is called a "ring". An image processing algorithm tailored to enhancement of irregularly-shaped rings is considered to be adapted to classification of reactions in which the cell membrane is the transposition site. Such reactions may be called membrane activation responses. An image processing algorithm for analyzing images of cells undergoing membrane activation may be termed a membrane activation image processing algorithm. However a membrane activation algorithm may not be effective in enhancing the visualization of lipid droplets within cells. As is known, adipocytes (the cell type that composes fat tissue) feature lipid droplets within the cells that represent the main storage depot of fat. Similar lipid droplets are also found in other cell types, including but not limited to muscle cells, 3T3L1 and HeLa cells, and Chinese Hamster Ovary cells. Lipid droplets are spherically-shaped, lipid-containing objects whose outlines are not effectively enhanced by algorithms adapted for the irregularly-shaped rings. Instead, an image processing algorithm adapted to enhance the regular circular outline of lipid droplets would be useful in supporting measurements of cells to responses related to lipid metabolism. Such an algorithm may be called a lipid droplet image processing algorithm.

SUMMARY OF THE INVENTION

A system and method for processing an original image of biological material to identify certain components of a biological object locates the biological object in the image, enhances the image by sharpening components of interest in the object, and applies a contour-finding function to the enhanced image to create a contour mask. The contour mask may be processed to yield a segmented image, that is, an image in which pixels representing the biological object have been subclassified (or assigned) to structural regions of the cells (e.g., nucleus, plasma membrane, cytoplasm, lipid droplet).

A kit for obtaining images of biological material stimulated to elicit a particular response includes a plurality of reagents for fixing and staining the stimulated material and a program product adapted for segmenting an image of the stimulated material.

BRIEF DESCRIPTION OF THE DRAWINGS

FIG. 3B illustrates a flowchart implementing an exemplary embodiment of the process of FIG. 3A.

FIG. 4A illustrates parameters of an exemplary model of membrane selective filtering for an edge enhancement algorithm. FIGS. 4B and 4C depict examples of linear filter values for the exemplary model of membrane selective filtering that tests local linearity of pixel neighborhoods in a magnified image to produce an enhanced image.

FIG. 5A depicts a magnified image of biological material in which cells have been activated, fixed, and stained. FIG. 5B is an enhanced image obtained by processing the image of FIG. 5A to improve the presentation of cell components. FIG. 5C is a mask derived from application of marks to the enhanced image.

FIGS. 6A-6J constitute a sequence of images that illustrate operation of the automated imaging process of FIGS. 3A implemented with the exemplary embodiment of FIG. 3B.

FIG. 8 illustrates a flowchart representing an automated imaging process to identify components of a biological object in an original image of human fat cells.

FIGS. 9A-9L constitute a sequence of images that illustrate operation of the automated imaging process of FIG. 8.

DETAILED DESCRIPTION OF THE PREFERRED EMBODIMENTS

In this specification, the components to be identified are surface and/or structural features in magnified images of cells. The features are useful in enabling an automated image process to distinguish structures such as individual cells and/or components of cells in a digital image in order to obtain information useful in making measurements. An automated image process is a stream of activity conducted by a machine or capable of being conducted by a machine that processes information in a digital image. The components of interest are those features in an image that represent some shape, structure, form, or appearance of all or a part of a surface and/or a structure of cellular material. Examples of such components include, as examples and without limitation, boundaries between cells, outlines of cell membranes, outlines of intracellular membranes, and boundaries and/or outlines of intracellular objects. The automated image process may be executed by an automated high-throughput microscopy system that automatically generates sequences of magnified images by well known automated means or by an automated single-microscope system including a camera and digital processor that obtains images in response to user prompts.

In image processing, the act of distinguishing is sometimes referred to as "segmentation", which, according to J. C. Russ, *The Image Processing Handbook*, (CRC Press, 1992) at page 225, is "dividing the image up into regions that hopefully correspond to structural units in the scene or distinguish objects of interest". In cytometry, "structural units" may include, without limitation, nuclei, membranes, rings on lipid droplets, and other features. The "hopefully" qualification of Russ' definition attests to the difficulty encountered by an automated image process in determining what the regions are. The difficulty is reduced to the extent that an image process is enabled to identify cellular components in order to distinguish objects in a digital image of magnified biological material.

A method for processing an original image of biological material to identify components on a surface or in a structure of a biological object may be implemented in a software program written in the C++ and Java programming languages and a counterpart system may be a general purpose computer system programmed to execute the method. Of course, the method and the programmed computer system may also be embodied in a special purpose processor provided as a set of one or more chips. Further, there may be a program product constituted of a program of computer instructions stored on a tangible article of manufacture that cause a computer to execute the method. The tangible article of manufacture may be constituted of one or more portable storage devices such as magnetic or optical disks or it may be constituted of a node in a network.

Figure 1:
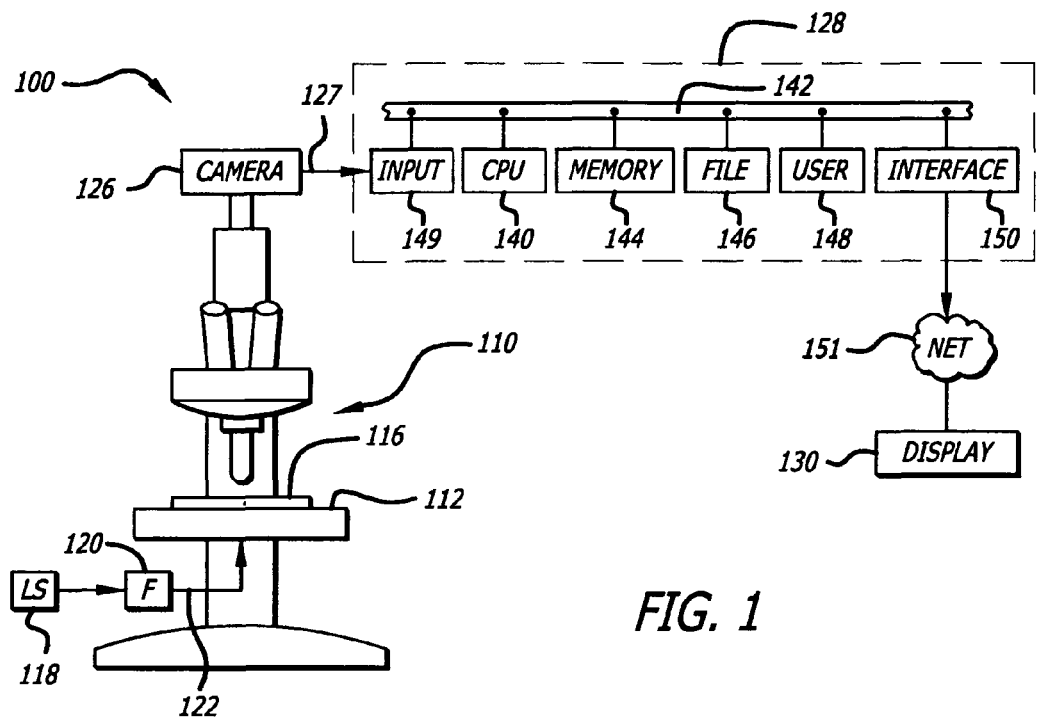
FIG. 1 illustrates an automated microscopy system for obtaining and processing an image of biological material to identify components in a biological object in the image.
Figure 7:
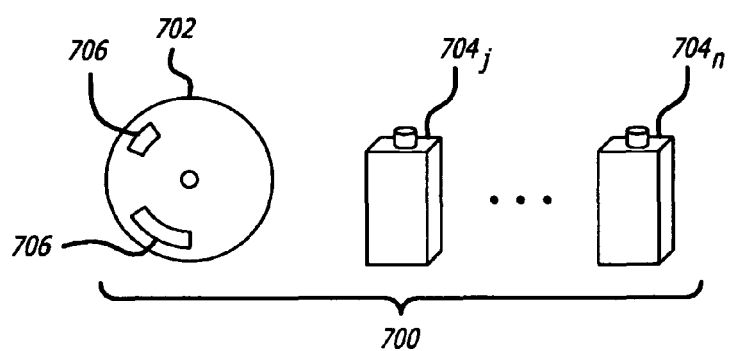
FIG. 7 illustrates a kit to facilitate measurements of activity in biological material.

FIG. 1, which is meant for example and not for limitation, illustrates an automated microscopy system 100 including a microscope 110 with a motorized, automatically moveable stage 112 on which a carrier 116 of biological material may be disposed for observation by way of the microscope 110. The material may be live cells, or it may be cells that have been fixed. The carrier 116 may be a slide with a single container, or it may have a plurality of containers. For example, and without limitation, the carrier 116 may be a ninety-six well micro-titer plate in each well of which there is biological material that has been cultured, activated, fixed, and stained. A light source 118 provides illumination for operation of the microscope 110 by way of an optical filter 120 and a fiber optic cable 122. The moveable stage 112 may be stationary to obtain a single image, or it may be intermittently or continuously moved to enable the acquisition of a sequence of images. Images observed by the microscope 110 are directed by mirrors and lenses to a high-resolution digital camera 126. The camera 126 obtains and buffers a digital picture of a single image, or obtains and buffers a sequence of digital pictures of a sequence of images. A digital image or a sequence of digital images is transferred from the camera 126 on an interface 127 to a processor 128. The interface 127 may be, for example and without limitation, a universal serial bus (USB). Digital images may be in some standard format that is received as, or converted into, original, magnified images, each composed of an N×M array of pixels by the processor 128. The processor 128 receives one or more original, magnified digital images of biological material and stores the images in image files. The original digital images are processed by the processor 128 and output digital images are provided by the processor 128 for display on an output device with a display 130.

With further reference to FIG. 1, the processor 128 may be a programmed general purpose digital processor having a standard architecture, such as a computer work station. The processor 128 includes a processing unit (CPU) 140 that communicates with a number of peripheral devices by way of a bus subsystem 142. The peripheral devices include a memory subsystem (MEMORY) 144, a file storage subsystem (FILE) 146, user interface devices (USER) 148, an input device (INPUT) 149, and an interface device (INTERFACE) 150.

The bus subsystem 142 includes media, devices, ports, protocols, and procedures that enable the processing unit 140 and the peripheral devices 144, 146, 148, 149, and 150 to communicate and transfer data. The bus subsystem 142 provides generally for the processing unit and peripherals to be collocated or dispersed The memory subsystem 144 includes read-only memory (ROM) for storage of one or more programs of instructions that implement a number of functions and processes. One of the programs is an automated image process for processing a magnified image of biological material to identify one or more surface components of an object in the image, as explained in more detail below. The memory subsystem 144 also includes random access memory (RAM) for storing instructions and results during process execution. The RAM is used by the automated image process for storage of images generated as the process executes. The file storage subsystem 146 provides non-volatile storage for program, data, and image files and may include any one or more of a hard drive, floppy drive, CD-ROM, and equivalent devices The user interface devices 148 include interface programs and devices for entry of data and commands, initiation and termination of processes and routines and for output of prompts, requests, screens, menus, data and results.

The input device 149 enables the processor 128 to receive digital images from the camera 126. The interface device 150 enables the processor 128 to connect to and communicate with other processors, computers, servers, clients, nodes and networks. For example, the interface device 150 may provide access to the output device 130 by way of an internal network 151.

Figure 2:
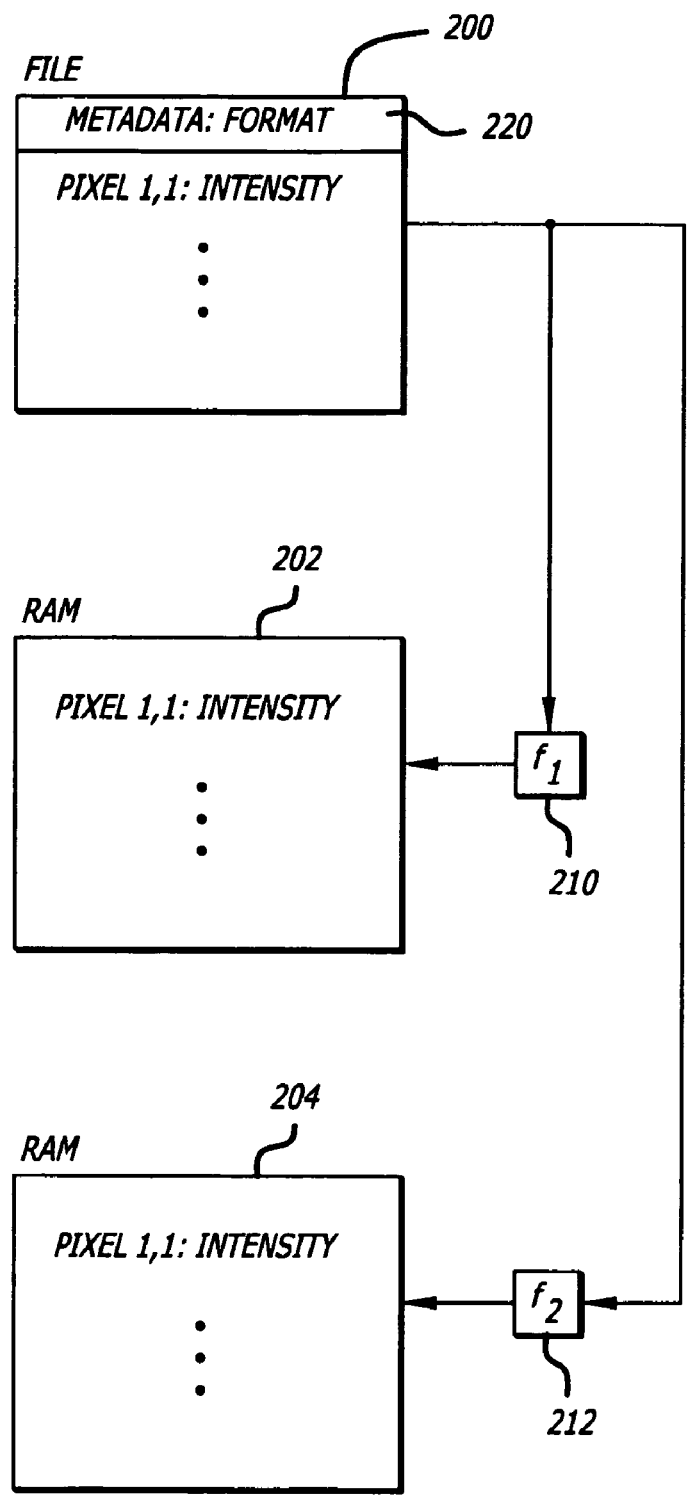
FIG. 2 illustrates data structures for storing images of biological material.

An automated image process obtains, processes and stores images of biological material. With reference to FIGS. 1 and 2, each original magnified image of biological material is obtained by moving the motorized stage 114 to position a sample of stained biological material in a focal plane of the microscope. The filter 120 is set by manual or automatic means to filter light produced by the light source 118 in order to illuminate the biological material in the field with light of a particular wavelength or waveband. The wavelength or waveband is selected in order to distinguish components that have absorbed a particular stain from other, differently stained components and from unstained components. An original image is one obtained by the camera 126 from the microscope 110 and stored in a file 200 in the file storage subsystem 146. Intermediate images are obtained by processing original and/or other intermediate images. For example one intermediate image 202 may be obtained by subjecting an original image to a normalization step 210, while another intermediate image 204 may be obtained by subjecting the same original image to a filtration step 212. The file 200 may have any format appropriate to storage of image data. For example, the structure of the file 200 may include image metadata 220 and a sequence of pixels, in scan order (x,y), where each pixel is a digital number representing intensity. The data structures for intermediate images correspond to those of original images. Images are staged to RAM for temporary storage of processing results and also for output to the display device 130.

An automated image process may be classified according to the response that it is adapted to obtain information from. For example and without limitation, there may be an automated image process adapted for membrane activation and an automated image process adapted for analysis of lipid droplets. Each such automated image process may be utilized to process one image of interest, or may process multiple images streamed to the process in a sequence. For simplification, but without limitation, these processes will be described as processing a single image; supplementary program means for preparing images to be processed and for controlling a flow of images to the automated image process are well within the scope of the art. Therefore, only elements of the automated image processes will be described.

Membrane Activation Image Process

Presume that one or more original magnified images of material stimulated to produce a membrane activation response are obtained. Presume further that materials transposing to or from the cell membranes have been stained with a first stain fluorescing at one wavelength of light and that the nuclei have been stained with second stain, fluorescing at a different wavelength of light. The objective of a membrane activation image processing algorithm is to identify the probable location of cell membranes within the stained image, in order to reliably segment (or subclassify) the image into regions corresponding to the cytoplasm, plasma membrane, or nucleus of the cells. Preferably, the membrane activation algorithm consists of two steps: membrane segmentation and membrane measurement. Membrane segmentation locates the pixels in the magnified original image that belong to the cell membrane; membrane measurement uses the pixels in the cell membrane to obtain information from the magnified original image relative to values for one or more parameters. The algorithm needs to be capable of detecting the membrane in areas of the image where it is stained; if staining of the membrane is incomplete, the algorithm needs to be able to accurately infer the location of the membrane from the local staining pattern. Membrane measurements may then be computed on classified pixels. For example, and without limitation, knowing the pixels in the cell membrane enables the determination of a total number of cells in the original magnified image, and the location of pixels corresponding to the plasma membrane and cytoplasmic regions of the cells. For example, and without limitation, knowing the pixels in the cell membrane enables the determination of a total number of cells in the original magnified image.

Figure 3A:
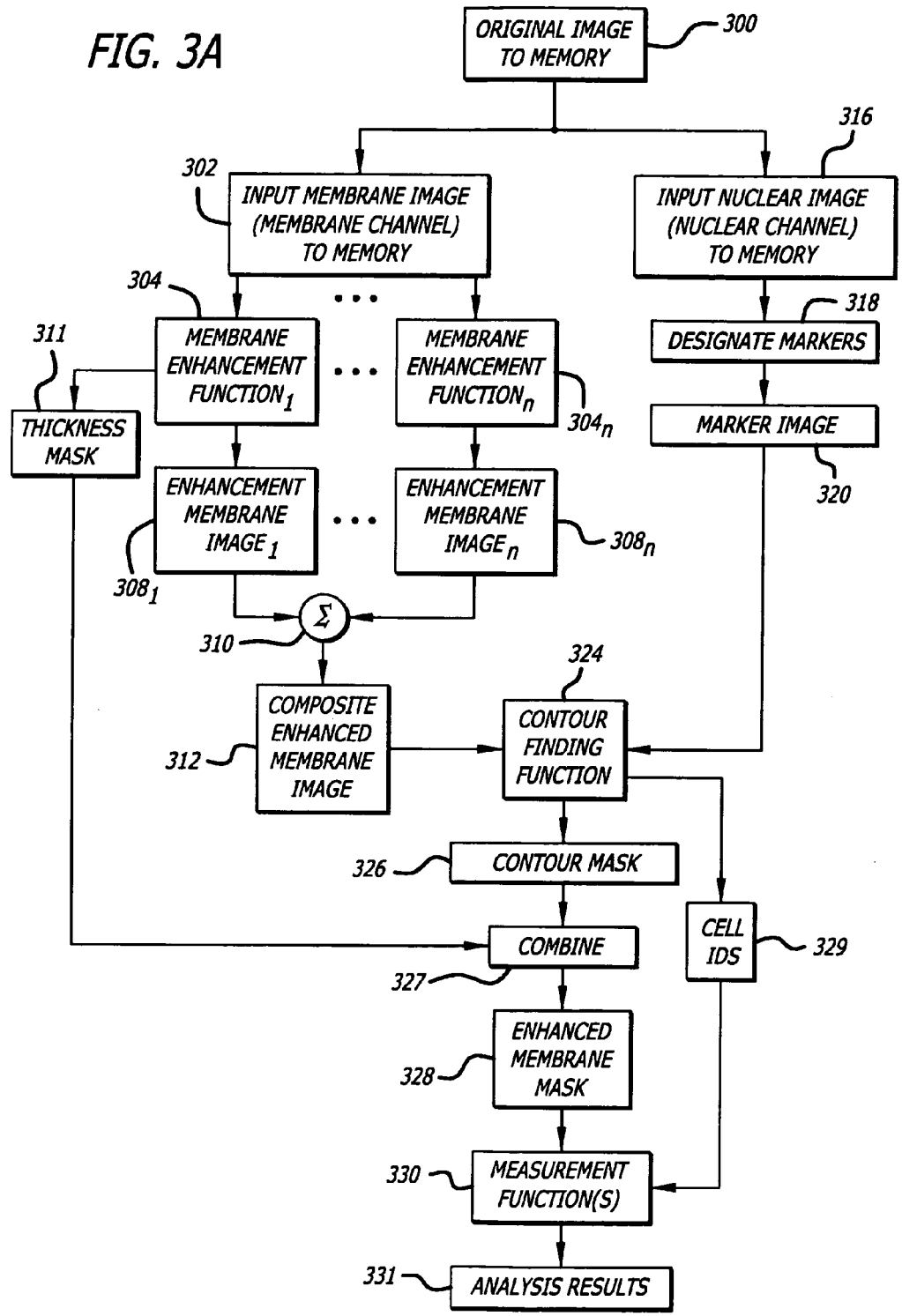
FIG. 3A illustrates a flowchart representing an automated imaging process to identify components of a biological object in an original image of biological material.

FIG. 3A illustrates a membrane activation image process that may be performed by a programmed digital computer in a system such as the automated microscopy system of FIGS. 1 and 2, or a special purpose processor in which at least one original magnified image of stained biological material, preferably containing cells, is obtained and processed. Presume that the biological material has been stained with a membrane stain and a nuclear stain. Presume further that the membrane stain has an affinity for an enzyme that transposes to cell membranes when stimulated, which causes the membranes of the cellular material to be visible when illuminated with a certain (first) wavelength or waveband of light (which may be called the "membrane channel"). An image obtained by the system of FIG. 1 through the membrane channel may be termed a "membrane image". The nuclear stain causes the nuclei of the cellular material to be visible when illuminated with another (second) wavelength or waveband of light (which may be called the "nuclear channel"). An image obtained by the system of FIG. 1 through the nuclear channel may be termed a "nuclear image". Membrane and nuclear stains are available in "labeling kits".

In FIG. 3A, step 302, an input membrane image is obtained and stored. The membrane image is processed by at least one enhancing function; preferably the membrane image is processed by two or more enhancing function, represented by function $304_1$ through function $304_n$. An enhancing function enhances the membrane image to emphasize some feature or features of the image. For example, and without limitation, one enhancing function may emphasize the linear structures of the membrane outlines, while another enhancing function may emphasize the contrast between background pixels and pixels in the membrane outlines. Each enhancing function produces an enhanced membrane image. In FIG. 3A, the enhancing function $304_1$ produces an enhanced membrane image $308_1$ and the enhancing function $304_n$ produces an enhanced membrane image $308_n$. The enhanced membrane images may be combined by algebraic weighted summation 310. The algebraic summation 310 produces a composite enhanced membrane image 312 that is placed in temporary storage for further processing.

In FIG. 3A, at least one enhancing function produces a membrane thickness mask. For example, the membrane enhancement function $304_1$ produces a membrane thickness mask 311. A mask is an image with one or more outlines in which each outline restricts the analysis of another image (such as the original membrane image) to an area contained within the outline. A membrane thickness mask is a mask that contains one or more outlines of cell membranes that have thickness corresponding to the thickness of corresponding outlines in the input membrane image 302.

Continuing with the explanation of FIG. 3A, an input nuclear image is obtained and stored in step 316 and elements in the nuclear image are designated as markers in step 318. The result of the designation is a marker image 320. In step 324, the markers in the marker image are applied by a contour-finding function to the enhanced membrane image 312 to generate a contour mask in step 326. One group of well-known contour-finding functions that separates overlapping and/or touching outlines includes "watershed algorithms"; another includes "active contour" algorithms. See, for example, J. C. Russ, op cit., at pp. 328-336. In the contour mask, the membrane outlines, including overlapping and/or touching outlines typically have a fixed width. For example, the membrane outlines may be one pixel wide. The pixels in the membrane outlines are assigned a fixed, high ("on") intensity value while the remaining pixels are assigned a fixed, low ("dark") intensity value. The resulting contour mask is a precise and distinct trace of the membrane outlines, but it may omit variation in membrane thickness that is present in the input image. In order to thicken the outlines so that they more accurately portray membrane outlines in the input image, the thickness mask 311 with membrane thickness information may be combined with the contour mask 326 by a reconstruction algorithm in step 327. The product of step 327 is a segmented membrane image in the form of an enhanced membrane mask 328. The enhanced membrane mask is placed in memory in step 328.

The contour finding function in step 324 also produces a list or table of spaces contained within the contour mask 326. The list or table uniquely identifies each space with respect to all other identified spaces. As will be evident, these spaces correspond to the cells in the original image. Therefore, the list or table of identified spaces may be used as a list or table of cell identifications (CELL IDS) in step 329. The CELL IDS list or table 329 is stored in association with the enhanced membrane mask 328.

The enhanced membrane mask 328 and the CELL IDS 329 in memory may be utilized by one or more measurement functions in step 330 to produce analysis results in step 331. Such results may include one or more of the measurement calculation results listed in Table I.

TABLE I

MEMBRANE ACTIVATION ANALYSIS MEASUREMENTS

Cell Count
Cell Dimensions
Membrane Area
Membrane Dimensions
Membrane Intensity
Cytoplasm Area
Cytoplasm Dimensions
Cytoplasm Intensity
Nuclear Area
Nuclear Intensity
Median Intensity Ratios (Membrane, Cytoplasm, Nuclear)
Median Intensity Differences (Membrane, Cytoplasm, Nuclear)

FIG. 3B illustrates an exemplary embodiment of the membrane activation image process of FIG. 3A with at least one, and preferably two or more enhancement functions, each of which improves or emphasizes the portrayal of membrane outlines with respect to other features in an input image. The first enhancement function, comprising steps 30410-30419, emphasizes the trace and thickness of membrane outlines. In more detail; the first enhancement function may be one that locates bright thin structures in images that correspond to membrane segments in cases where a membrane stain is visible in the input membrane image. The second enhancement function, comprising steps 30420-30429, finds a cell-background boundary by enhancing contrast between pixels in the cells and those outside of the cells. Preferably, the enhancement functions emphasize different aspects of membrane appearance. One enhancement function enhances the membrane outline where the stained membrane outline is visible, while a second enhancement function enhances the membrane outline where the stained membrane might not be visible but where a membrane outline may be visible against a background. In the first enhancement function, the input image is normalized in step 30410 by a function that transforms the scale of pixel values in all parts of the image in a uniform manner such that the full range of values available are utilized. Next, in step 30412, a membrane enhancement algorithm is applied to the normalized image produced in step 30410. The enhancement algorithm locates and amplifies the membrane outlines in the normalized image. Then, in step 30414 a dynamic thresholding algorithm is applied to the normalized, membrane enhanced image produced in step 30412. The dynamic thresholding algorithm compares the intensity values of the pixels in the membrane outlines to a threshold value and turns off pixels that fail the test by setting their intensity value to a background value. The threshold is dynamic in that it is continuously recalculated in reaction to changes in the distribution of intensities in a brightness histogram. The output of step 30414 is a mask 30415 that may be used as the thickness mask of FIG. 3A. In step 30416, a constrained distance procedure is applied to the mask 30415 produced by step 30414. The constrained distance procedure computes the distance of each background pixel from the nearest pixel in a membrane outline and assigns a brightness value to the pixel having a magnitude equal to the measured distance. That is to say, the further a pixel is from a membrane outline, the brighter it is. If the distance is greater than a fixed number, the pixel magnitude is set to that number, therefore the distance calculation is constrained to a maximum value. Then, in step 30418, all pixels are inverted in brightness value. The desired effect of inversion is to enhance the continuity of the membrane outlines by turning on pixels that lie in gaps of membrane outlines. The output of the sub-sequence 30416, 30418 is an enhanced membrane image 30419 in gray scale form that contains enhanced membrane outlines with thickness information. The enhanced membrane image 30419 is weighted by a weight $a_1$ and input to the algebraic summation step 310. One undesirable effect of the sub-sequence 30414, 30415 is the creation of bright spots in the mask 30415 that are not part of or connected to membrane outlines. However, these are eliminated by the combining step 327 of FIG. 3A when the contour mask 326 is combined with the mask 30415. In this regard, presuming use of a watershed function in step 324 that produces a contour mask 326 with pixel-wide membrane outlines, the processing of the combining step 327 follows the membrane outlines of the contour mask, thickening them where they correlate with thicker lines in the mask 30415, and dispensing with bright portions of the mask 30415 that do not touch the membrane outlines.

Continuing with the description of FIG. 3B, the second enhancement function provides complimentary location information in cases where cells are not densely packed and intercellular spaces are present in the input image. In the second enhancement function, the input image is normalized in step 30420. Next, in step 30422, a segmentation algorithm (such as a background subtraction algorithm) is applied to the normalized image produced in step 30420 to segment cells from the background. Then cell outlines are found from the cell masks (for example by erosion and subtraction A constrained distance/inversion sub-sequence comprising steps 30426, 30428 (and corresponding to 30416, 30418) is applied to the mask 30425 produced by step 30424, which produces an enhanced membrane image 30429. The enhanced membrane image contains membrane outlines with enhanced contrast against the background. The enhanced membrane image 30429 is weighted by a weight $a_2$ and input to the algebraic summation step 310.

In the exemplary embodiment of FIG. 3B, the input membrane image is normalized in step 3051. The normalized input membrane image produced by step 3051 is weighted by a weight $a_n$ and input to the algebraic summation step 310. The weighted, normalized input membrane image may be selectively summed with zero, one, more than one, or all of the gray scale enhanced membranes images output by the membrane enhanced algorithms to produce a composite enhanced membrane image (312 of FIG. 3A). The remainder 3052 of the exemplary embodiment membrane activation image process executes as per steps 312-330 of FIG. 3A.

When present in an image, a membrane outline can be viewed as a locally linear phenomenon because every small section of a membrane outline or outline fragment appears in a local neighborhood as a bright line or low-order curve against a less bright background. Tis property is not directly accessible by, for example, thresholding the input image, because the dynamic range of the background and membrane outline can vary widely across the field of view. However, filters may be constructed whose response is selective for locally linear structures in a membrane image insensitive to absolute variations in background or membrane signal intensity, and threshold rectification of such preferentially enhanced structures can produce binary images that reliably localize the visible membrane locations across the image. Thus, the exemplary filter embodiment of FIG. 3B is based on a model of selective filtering for locally linear structures (step 30412), followed by threshold rectification (30414) to create a binary membrane mask image (30415). The filters can be constructed from a variety of techniques. One exemplary implementation may use a bank of paired oriented linear filters, but linear or nonlinear alternatives such as Gaussian filters or Difference of Gaussian filters described in Malik and Perona (1990) and elsewhere could also be used. The paired, oriented linear filters come in two matched banks, left and right, and may be tuned to a user programmable set of orientations $\theta$, for example $\theta \in \{0, \pi/6, \pi/3, \pi/2, 2\pi/3, 5\pi/6\}$. Although membrane structures occur over a continuum, in practice because the input membrane image is digitized and the membrane activation image process operates at a finite resolution, a discrete set of tuned filters produces adequate response and there is usually little improvement over six orientations. For each orientation, the left and right filter responses are computed and subtracted with zero saturation (nonnegative output image) from the input membrane image (302), then the membrane response is calculated as the pixelwise minimum (morphological intersection) of the differences:

$$R(x) = \min\{I(x) - f_{left}^\theta(I(x)), I(x) - f_{right}^\theta(I(x))\}$$

Left and right filter responses are constructed as a pair to respond to the presence of high image intensity, relative to a central target pixel, on the left and right of the target with respect to the filter pair orientation. An analytical representation of these filters with orientation $\theta$ in 2D space spanned by vector x with parameters $L_1, L_2, L_3$ and rotation matrix $R(\theta)$ is:

$$f_{left}^{\theta}(x) = \begin{cases} a & \|[R(\theta)x]_2\| \le L_1 \\ & -L_3 \le [R(\theta)x]_1 \le -L_2 \\ 0 & \text{otherwise} \end{cases}$$

$$f_{right}^{\theta}(x) = \begin{cases} a & \|[R(\theta)x]_2\| \le L_1 \\ & L_2 \le [R(\theta)x]_1 \le L_3 \\ 0 & \text{otherwise} \end{cases}$$

$$R(\theta) = \begin{bmatrix} \cos\theta & \sin\theta \\ -\sin\theta & \cos\theta \end{bmatrix}$$

where a is selected to normalize the filter response $\iiint f(x)dx=1$. Digital versions of these filters can be constructed by the following edge enhancement algorithm:

```
START
for each θ,
    /* initialize */
    n ← 0
    f_left^θ[i, j] ← 0
    f_right^θ[i, j] ← 0
    /* turn positive response area on for both filters */
    for each column j,
        for each row i, compute x' = R(θ)[i/j]

if ‖x'_2‖ ≤ l_1
                if -L_3 ≤ x'_1 ≤ -L_2
                    f_left^θ[i, j] ← 1
                    n = n + 1
                endif
                if L_2 ≤ x'_1 ≤ L_3
                    f_right^θ[i, j] ← 1
                endif
            endif
        end for i
    end for j
    /* normalize to unity response */
    f_left^θ[i, j] ← f_left^θ[i, j]/n
    f_right^θ[i, j] ← f_right^θ[i, j]/n
end for θ
END
```

Figure 4C:
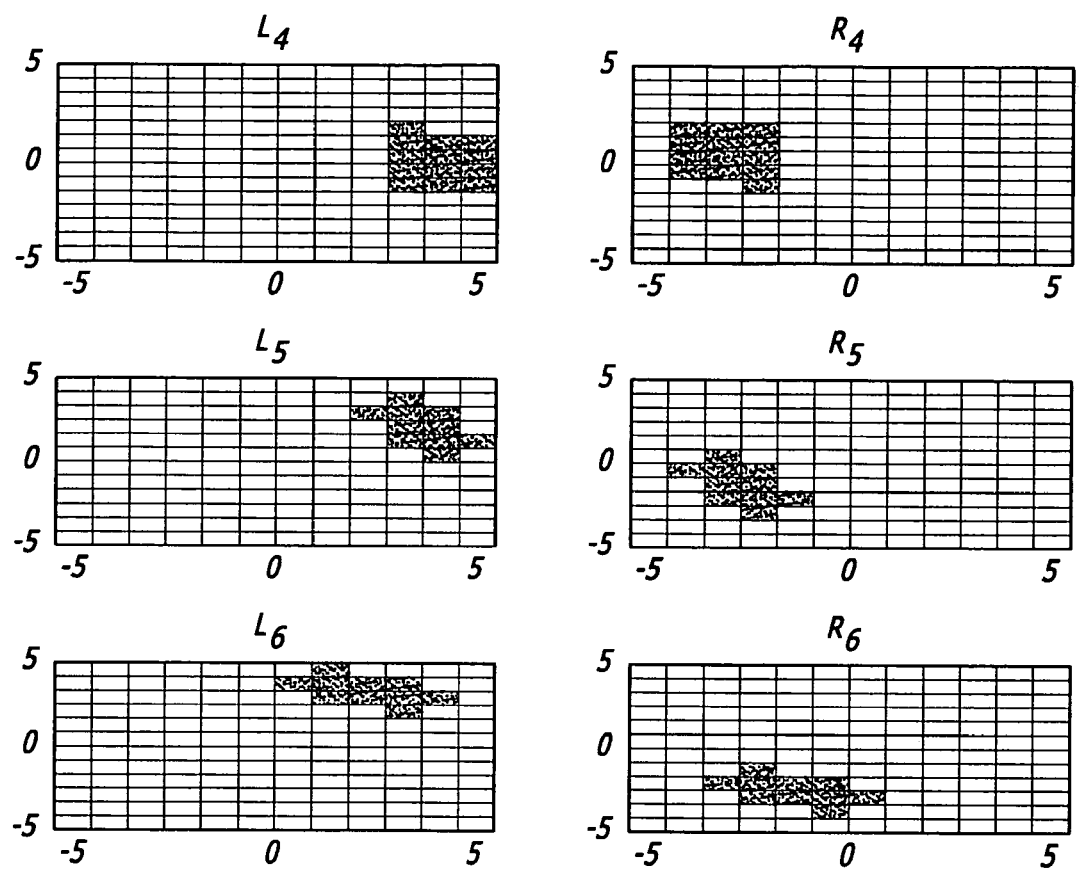

The parameters of the edge enhancement algorithm set forth above are illustrated in FIG. 4A. These parameters are interpreted with reference to FIG. 4A as follows. $L_1$ is the half-length of the response in the direction $\theta$, $L_2$ and $L_3$ are the inner and outer boundaries of the response in the direction orthogonal to $\theta$ that together define the response width. Plots of the response of example digital filters with $L_1$=2, $L_2$=3 and $L_3$=5 are shown in FIG. 4B for $\theta \in \{0, \pi/6, \pi/3\}$ and in FIG. 4C for $\theta \in \{\pi/2, 2\pi/3, 5\pi/6\}$.

The operation of the membrane activation image process of FIG. 3A, in the case implemented with the exemplary embodiment of FIG. 3B, may be represented by FIGS. 5A, 5B, and 5C. FIG. 5A depicts an original magnified image of biological material in which cells have been activated, fixed, and stained. This may constitute the image 300 that is input to the membrane activation image process of FIG. 3A. FIG. 5B depicts a composite enhanced membrane image obtained by processing the image of FIG. 5A according to step 312 of FIG. 3A to improve the presentation of membrane outlines. FIG. 5C is a contour mask derived from the image of FIG. 5A by using a watershed algorithm as the contour finding function in step 324 of FIG. 3A, with stained nuclei of the input nuclear image designated as markers for the watershed algorithm.

For an understanding of results obtained during the operation of the membrane activation image process according to FIG. 3A and the exemplary embodiment of FIG. 3B in which the contour finding function in step 324 is implemented as a watershed function, consider FIGS. 6A-6J. In these figures, certain features are shown in color only to emphasize the appearance of those features. In the exemplary instance using the watershed algorithm, the choice of markers depends on the distribution of cells in the original image (300 in FIG. 3A). If the cells are confluent, the nuclear image of step 316 in FIG. 3A the visible nuclei in the nuclear image are sufficient markers. However, if the cells are sparse, an additional marker is needed to construct a watershed basin for the background. This additional marker may be designated as the background marker. A background may be defined as a collection of local maxima of distance from the nuclei. In practice this can be calculated as a collection of watershed lines for the watershed algorithm, applied to a flat image using nuclei as markers. FIG. 6A depicts an input membrane image as might be present in step 302 of FIG. 3A. FIG. 6B illustrates a nuclear image as might be present in step 316 of FIG. 3A. FIG. 6C illustrates designation of nuclei as markers according to step 318 of FIG. 3A, overlaid on the membrane channel image of FIG. 6A. FIG. 6D shows a normalized input membrane image as might be present in steps 30410, 30420, and 30451 of FIG. 3B. FIG. 6E illustrates the output of the edge enhancement algorithm at step 30412 as practiced according to the pseudo-code set forth above. In FIG. 6F, a mask produced from the output of the edge enhancement algorithm by dynamic thresholding according to step 30414 of FIG. 3B is shown. As may be appreciated with reference to FIG. 6F, the mask comprises a membrane outline constituted of segments of varying thickness and continuity with bright spots interspersed throughout the image. FIG. 6G shows the membrane mask of FIG. 6F after being subjected to the constrained distance procedure of step 30416 in FIG. 3B. In FIG. 6H, an enhanced membrane image in gray scale format derived from inversion of the image in FIG. 6G is illustrated. FIG. 6I shows a contour mask (representative of a contour mask in step 326 of FIG. 3A), with markers, derived from the nuclear markers in the image of FIG. 6C according to a watershed algorithm in step 324 of FIG. 3A. In FIG. 6I, the nuclear markers are in red and the contour lines representing a membrane outline are in green. The final membrane mask (step 328 of FIG. 3A) is illustrated in FIG. 6J.

Two further applications of these processing steps are described further here. Firstly, the membrane signal may be used to improve segmentation of multi-nucleated cells, such as cells that undergo nuclear division but fail in the cytokinesis stage of cell division that can occur in a variety of human diseases. In this case, each adjacent pair of cells can be examined for membrane strength on the line separating two cells. Two measurements for membrane strength from many possibilities could be a pixel count in the membrane mask 311 or the average membrane intensity along this membrane signal path. A second application of the processing steps in this application could be to use the membrane signal to separate touching nuclei by not examining nuclear objects for strong lines in the membrane mask 311 that would have been discarded in step 327 of the principal application.

Membrane Activation Kits

PKC represents a family of enzymes that help regulate cell division and migration, processes that when improperly controlled lead to tumor growth and metastasis. When PKCα is activated, it transposes (migrates) from the cytoplasm to the plasma membrane where it interacts with regulators of the cell cycle and cell motility pathways. Modulators of PKC show potential as anti-tumor drugs and the idea that inhibitors of PKCα could serve as anti-cancer agents is a subject of intense interest. In order to determine whether a substance is effective in controlling PKCα, a cell line derived from a tumor may be stimulated by exposure to that substance and the result may be visualized in the form of a magnified image. To evaluate the result, one measurement of interest might be determination of the amount of PKCα transposed to the membrane on a per-cell basis. With staining, the PKCα is visible when illuminated at a particular wavelength. With accurate determination of membrane outlines by the above-described membrane activation image process, cells may be identified and the transposition of PKCα in each identified cell may be measured.

E-cadherins are widely distributed cell adhesion molecules that feature large extracellular domains at the membrane that bind to each other on neighboring cells in a zipper-like fashion. Intracellular domains of these cadherins bind to catenins, which, in turn, bind actin fibers in the cytoskeleton. The cadherin-cadherin interaction provides a mechanical linkage at the membrane between cells that is essential for proper differentiation, embryogenesis, and cell migration. In addition, cadherins participate in cell signaling, helping to couple mechanical stresses to regulatory molecules. Loss of E-cadherin expression at the membrane may generally promote invasiveness of tumor cells by reducing the interaction of cells with neighboring tissue. In addition, the displacement of E- with N-cadherin is observed in the progression of a number of cancers. To evaluate cadherin activity, one measurement of interest might be determination of the amount of N- or E-cadherin transposed to or from the membrane on a per-cell basis in response to a stimulus. With staining, N- or E-cadherin is visible when illuminated at a particular wavelength. With accurate determination of membrane outlines by the above-described membrane activation image process, cells may be identified and the transposition of N- or E-cadherin in each identified cell may be measured.

VE-cadherin contributes to the regulation of the cellular barrier function of human lung endothelial cells. When a person is infected with *Bacillus anthracis*, anthrax lethal toxin attacks that barrier function, causing hemorrhaging. A change in VE-cadherin distribution at the cell membrane may indicate a breakdown in the barrier function as an anthrax infection progresses. To evaluate activity of VE-cadherin in response to an anthrax infection, one measurement of interest might be determination of the amount of VE-cadherin transposed from the membrane on a per-cell basis in response to a stimulus. With staining, VE-cadherin is visible when illuminated at a particular wavelength. With accurate determination of membrane outlines by the above-described membrane activation image process, cells may be identified and the transposition of VE-cadherin in each identified cell may be measured.

In order to facilitate such measurements, a kit may be provided. The kit 700 in FIG. 7 is constituted of a program product 702 including a computer-readable storage medium that enables a computer or processor to perform a membrane activation image process as described above and one or more reagents represented by reagent containers 704$_1$-704$_n$ useful for enhancing the visibility of one or more substances to be transposed with respect to cell membranes. The program product 702 includes a medium suitable for storing a program of software instructions 706 that may be read, compiled and executed by a computer to perform a membrane activation image processing method such as that illustrated in FIGS. 3A and 3B. For example, the program product may include a programmed CD. The one or more reagents may include, without limitation chemical stains, molecular stains, immunolabels, and/or live or fixed stained cells.

For example, a kit for visualization of membrane activation may include:

a program product storing a program for a membrane activation image processing method such as that illustrated in FIGS. 3A and 3B;

a fixative constituted of a solution of 4% paraformaldehyde (weight/volume) prepared in phosphate buffered saline (0.144 g/L $KH_2PO_4$, 9.00 g/L NaCl, and 0.795 g/L $Na_2HPO_4$ (anhydrous) prepared in water), supplemented with 1 mM sodium hydroxide;

a permeabilizer constituted of 0.2% Triton X in PBS, with 0.02% sodium azide as a preservative;

a blocking buffer constituted of comprising a blocking solution of 10% goat serum, 3% bovine serum albumin (BSA, fraction V), and 0.02% sodium azide in PBS;

a primary antibody;

a secondary antibody;

a nuclear stain constituted of 10 mM Tris, 10 mM EDTA, 100 mM NaCl, 0.02% sodium azide, 150 ng/ml DAPI in water, pH 7.4.

In a kit for visualization of PKC, the stains may include, for example and without limitation, a primary antibody to PKCα such as rabbit polyclonal antibody to PKCalpha (available from Santa Cruz Biotechnology, catalogue sc-208), and a secondary antibody against rabbit antibody such as a fluorescein—conjugated goat-anti-rabbit antibody (e.g., Chemicon product number AP132F). Other secondary antibodies conjugated to fluorescent compounds including, but not limited to, TexasRed, Cy2, and Cy3 may also be used. Preferably, the primary antibody would be used in an approximate 1/100 dilution (optimized on a lot-by-lot basis) in the blocking buffer and the secondary antibody would be used in an approximate 1/1500 dilution (optimized on a lot-by lot basis).

In a kit for visualization of N-cadherin, the stains may include, for example and without limitation, a primary antibody such as Chemicon IHC2129 (a mouse-monoclonal antibody against N-Cadherin), and a secondary antibody such as a Texas-Red conjugated goat anti-mouse antibody (Jackson ImmunoResearch Laboratories, Inc 115-075-146). Preferably, the primary antibody would be used in an approximate 1/10 dilution (optimized on a lot-by-lot basis) in the blocking buffer and the secondary antibody would be used in an approximate 1/1500 dilution (optimized on a lot-by lot basis).

In a kit for visualization of E-cadherin, the stains may include, for example and without limitation, a primary antibody such as Chemicon IHC2123-6 (a mouse-monoclonal antibody against E-Cadherin), and a secondary antibody such as a Texas-Red conjugated goat anti-mouse antibody (Jackson ImmunoResearch Laboratories, Inc 115-075-146). Preferably, the primary antibody would be used in an approximate 1/10 dilution (optimized on a lot-by-lot basis) in the blocking buffer and the secondary antibody would be used in an approximate 1/1500 dilution (optimized on a lot-by lot basis).

In a kit for visualization of VE-cadherin, the stains may include, for example and without limitation, a primary antibody such as Chemicon MAB1989 (a mouse-monoclonal antibody against VE-Cadherin), and a secondary antibody such as a Texas-Red conjugated goat anti-mouse antibody (Jackson ImmunoResearch Laboratories, Inc 115-075-146). Preferably, the primary antibody would be used in an approximate 1/10 dilution (optimized on a lot-by-lot basis) in the blocking buffer and the secondary antibody would be used in an approximate 1/1500 dilution (optimized on a lot-by lot basis).

Lipid Droplet Image Process Obesity and diabetes are prevalent health risks in modern society, and these conditions are often linked to increased fat cell (adipocyte) number and lipid content. Adipogenic stem cells (preadipocytes) have been isolated from adult human donors via liposuction and cultured for further study by, for example, Zen-Bio, Inc. The process of adipocyte differentiation from the preadipocytes is marked by the appearance of triglyceride-containing lipid droplets in each cell. It would be desirable to be able to reliably visualize the structure of fat cells to evaluate processes and treatments of obesity and diabetes. For example, certain pharmaceuticals that activate peroxisome proliferator-activator receptors (e.g., PPARγ) have proven useful as anti-diabetic therapeutics (e.g., rosiglitazone), and this class of compounds stimulates lipid droplet formation in human adipocytes. Thus, a high throughput screen to quantify the effects of candidate pharmaceuticals on lipid droplet formation in adipocytes might help identify novel PPARγ—activating agents. Also, lipid droplets might be reduced in size by chemicals that interfere with lipogenesis; screening chemical libraries for agents with this effect might help identify potential dietary supplements that reduce human fat deposition.

However, lipid droplets in cells have a much more regular appearance than membrane rings and so are not easily or reliably visualized by edge-enhancement algorithms such as are disclosed above, as those image processes are adapted for visualization of the irregular shapes of membrane rings. Further, lipid droplets vary in size. Moreover, within certain regions of a cell, lipid droplets may be confluent, whereas other regions of the same cell may contain isolated lipid droplets. Further, lipid droplets may contain islands of confluent lipids in portions of the cell and isolated instances of single lipids in other portions. Desirably, a lipid droplets image process would be able to discern lipids in fat cells wherein one, some, or all of the above conditions are found. In this regard, FIG. 8 illustrates a lipid droplets image process that may be performed by a programmed digital computer in a system such as the automated microscopy system of FIGS. 1 and 2, or a special purpose processor in which at least one original magnified image of stained biological material, preferably containing lipid droplets, is obtained and processed to enhance the outlines of lipid droplets contained in the cell.

Presume that one or more original magnified images of fat cells are obtained. Presume further that lipids within the cells have been stained with a first stain and that the nuclei have been stained with second stain. The objective of a fat cell image processing algorithm is to enhance the shapes of fat cell lipids in order to reliably quantify information in the stained components. With reference to FIG. 8 and FIGS. 9A-9L, an original image of stained fat cells is processed by a lipid droplet image processing process. An original image of stained fat cells (such as the image shown in FIG. 9A) is received in step 802 and the image is processed by a band-pass filter in step 804, producing a filtered image such as the image shown in FIG. 9B. A histogram of the filtered image is generated in step 806 and a dynamic thresholding process based on the histogram is applied to the filtered image. Such an algorithm may implement the well-known Otsu threshold algorithm, for example. Step 806 produces a mask such as the mask shown in FIG. 9C. As may be appreciated with reference to FIG. 9C, the process steps 804, 806 are well adapted for finding isolated small lipid droplets, but do not reliably distinguish separate large lipid droplets. Accordingly, the input image is also input to step 808 where a histogram of the unfiltered image is generated and a dynamic thresholding process based on the histogram is applied to the filtered image. Such an algorithm may also implement the well-known Otsu threshold algorithm, for example. Step 808 produces a mask (such as the mask shown in FIG. 9D) in which isolated large lipid droplets are reliably distinguished but in which small droplets are not separated. The union of the two masks is taken at step 810, producing a composite mask such as that shown in FIG. 9E. As FIG. 9E shows clearly, a composite mask according to step 810 contains clustered lipid droplets (large and small), isolated small lipid droplets, and isolated large lipid droplets. A composite mask produced by step 810 is applied to the input image in step 812 to produce a cell image in which the outlines of lipid droplets are sharpened as compared to the input image presented to the process at step 802 and noise in the background is reduced; such an enhanced image is shown in FIG. 9F, which may be compared with FIG. 9A to appreciate the sharpening of large and small lipid droplets, alone and confluent. In step 814, small irregularities are eliminated from a masked image produced by step 812 by a morphological gray scale opening process. FIG. 9G shows the result of processing the masked image of FIG. 9F according to step 814. Markers for lipids are generated in step 816 by finding regional maxima. FIG. 9H shows markers generated according to step 816 applied to the image of FIG. 9G. If there is a background in the image being processed, a background marker is found in step 818 by applying watershed to a flat image using lipid markers, followed by step 820 in which portions of the generated background marker too close to lipids are removed. A background marker generated from FIG. 9G according to steps 818 and 819 is shown in FIG. 9I. In step 822, a gradient image is generated from the original image. A gradient image generated from the original image of FIG. 9A according to step 822 is shown in FIG. 9J. Then, in step 824, the gradient image produced in step 822 and the background and lipid droplet markers are fed to a contour-finding algorithm to produce a final lipid droplet mask 826 and a list or table of lipid droplet identifications 827. Such a contour-finding algorithm may include, for example and without limitation, a watershed algorithm. FIG. 9K shows the gradient image of FIG. 9J overlaid with the lipid droplet and background markers of FIGS. 9H and 9I. A final lipid droplet mask generated by a watershed algorithm from the images of FIGS. 9H-9J is shown in FIG. 9L. The final droplets mask and list or table of lipid droplet identifications produced by the contour-finding algorithm of step 824 are provided to one or more measurement functions in step 828. The measurement functions produce analysis results at step 830. The analysis results may include, for example and without limitation, lipid droplet count, lipid droplet area, lipid droplet intensity, and lipid droplet dimensions, as well as ratios and differences among lipid droplets and between lipid droplets and other cell components.

Figure 10B:
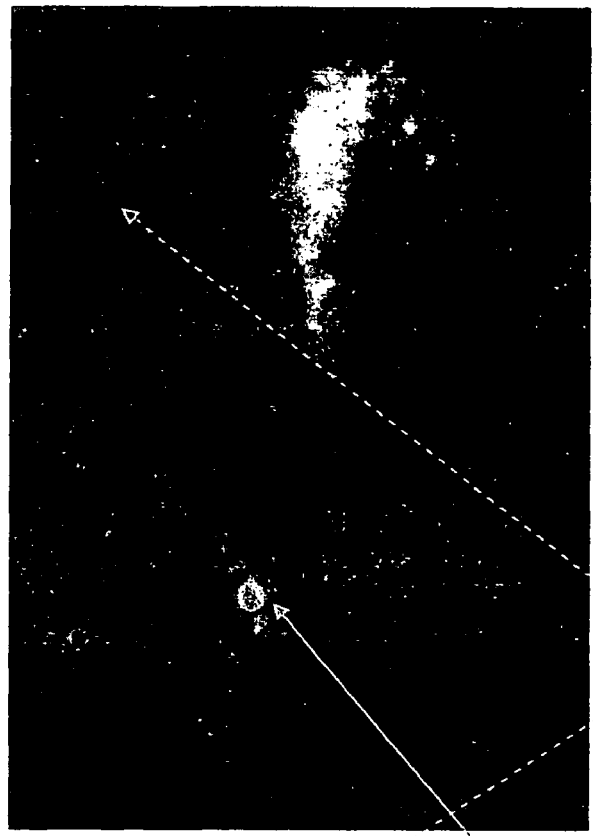
FIGS. 10A and 10B depict first and second channels obtained by staining biological material for lipid droplets and for perilipin, respectively.
Figure 10A:
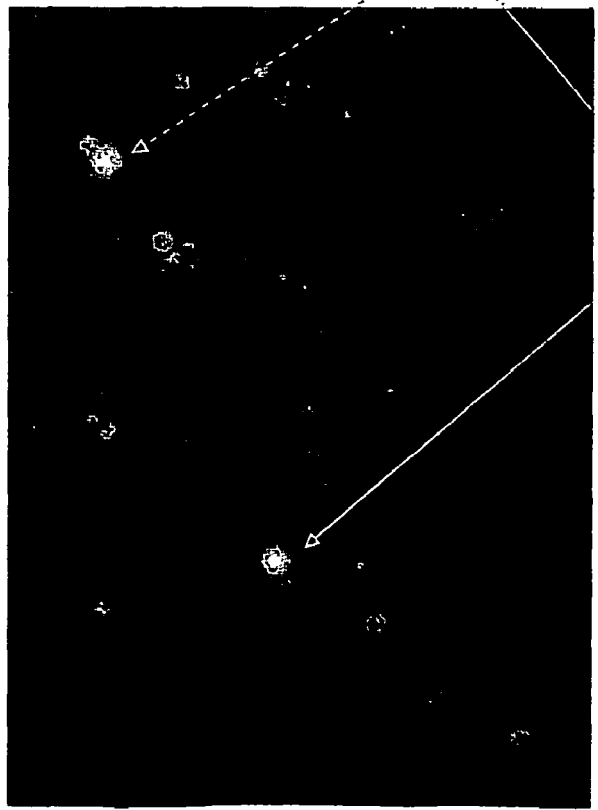

Lipid droplets are often surrounded by proteins and other molecules (for example, but not limited to, carbohydrates and lipids) that are often of interest. At early stages, the lipid droplets are coated with audiophile (also known as 'adipocyte differentiation related protein'); during maturation of the droplets, adipophilin is displaced by perilipin. Lipolysis in adipocytes is activated by beta-adrenergic stimulation, and the concomitant increases in cAMP and activation of protein kinase A (PKA). PKA-mediated phosphorylation of perilipin recruits Hormone Sensitive Lipase (HSL) to the lipid droplets, leading to lipolysis. Lipolysis also likely depends upon the recruitment to the lipid droplets of adipose triglyceride lipase (ATGL), a recently discovered lipase that is highly expressed in adipose tissue. It is desirable to measure cell features that are associated with lipid droplets. In this regard, proteins of interest, non-protein molecules of interest, or cellular structures of interest associated with the lipid droplets may be visualized and measured in separate optical channels through use of appropriate antibodies (both primary and secondary antibodies) or stains. For example, with reference to FIGS. 10A and 10B, lipid droplets are visualized by staining to establish a first (lipid) optical channel, while the protein perilipin can be visualized with a primary antibody (Research Diagnostics Incorporated Catalogue # PROGP29) and a secondary antibody in a second optical channel separate from the first optical channel. Thus, a lipid droplet at location 1000 is visible in the first optical channel of FIG. 10A and a ring of perilipin surrounding the lipid droplet at location 1000 is visible in the second optical channel. Similarly, a lipid droplet visible at location 1010 has no perilipin associated with it. Masks corresponding to proteins of interest (or non-protein molecules of interest, or cellular structures of interest) associated with the lipid droplets can be quantified by first subjecting the image acquired in the lipid droplet channel through the same lipid droplet analysis program described above. Secondly, the image corresponding to the protein of interest (or non-protein molecules of interest, or cellular structures of interest) associated with the lipid droplet can then be processed via the membrane activation algorithm, described above, using the lipid droplet mask instead of the nuclear mask to establish markers for the contour-finding function. The analysis results may include, for example, the percentage of total lipid droplets that are associated with the protein of interest, quantification of the intensity of staining of the protein of interest for droplets in which the protein of interest is associated, and analysis of the thickness of the contour corresponding to the protein of interest associated with the lipid droplets.

A kit for visualization of lipid droplets may include:
  a program product storing a program for a fat cell image processing method such as that illustrated in FIG. 8;
  a fixative constituted of a solution of 4% paraformaldehyde (weight/volume) prepared in phosphate buffered saline (0.144 g/L $KH_2PO_4$, 9.00 g/L NaCl, and 0.795 g/L $Na_2HPO_4$ (anhydrous) prepared in water), supplemented with 1 mM sodium hydroxide;
  a permeabilizer constituted of 0.1% Triton X in PBS;
  a blocking buffer constituted of comprising a blocking solution of 10% goat serum, 3% bovine serum albumin (BSA, fraction V), and 0.02% sodium azide in PBS;
  a lipid stain constituted of 1 µg/ml 4,4-Difluoro-1,3,5,7,8-pentamethyl-4-bora-3a,4a-diaza-s-indacene in blocking buffer; and
    a nuclear stain constituted of 10 mM Tris, 10 mM EDTA, 100 mM NaCl, 0.02% sodium azide, 150 ng/ml DAPI in water, pH 7.4.

Figure 11:
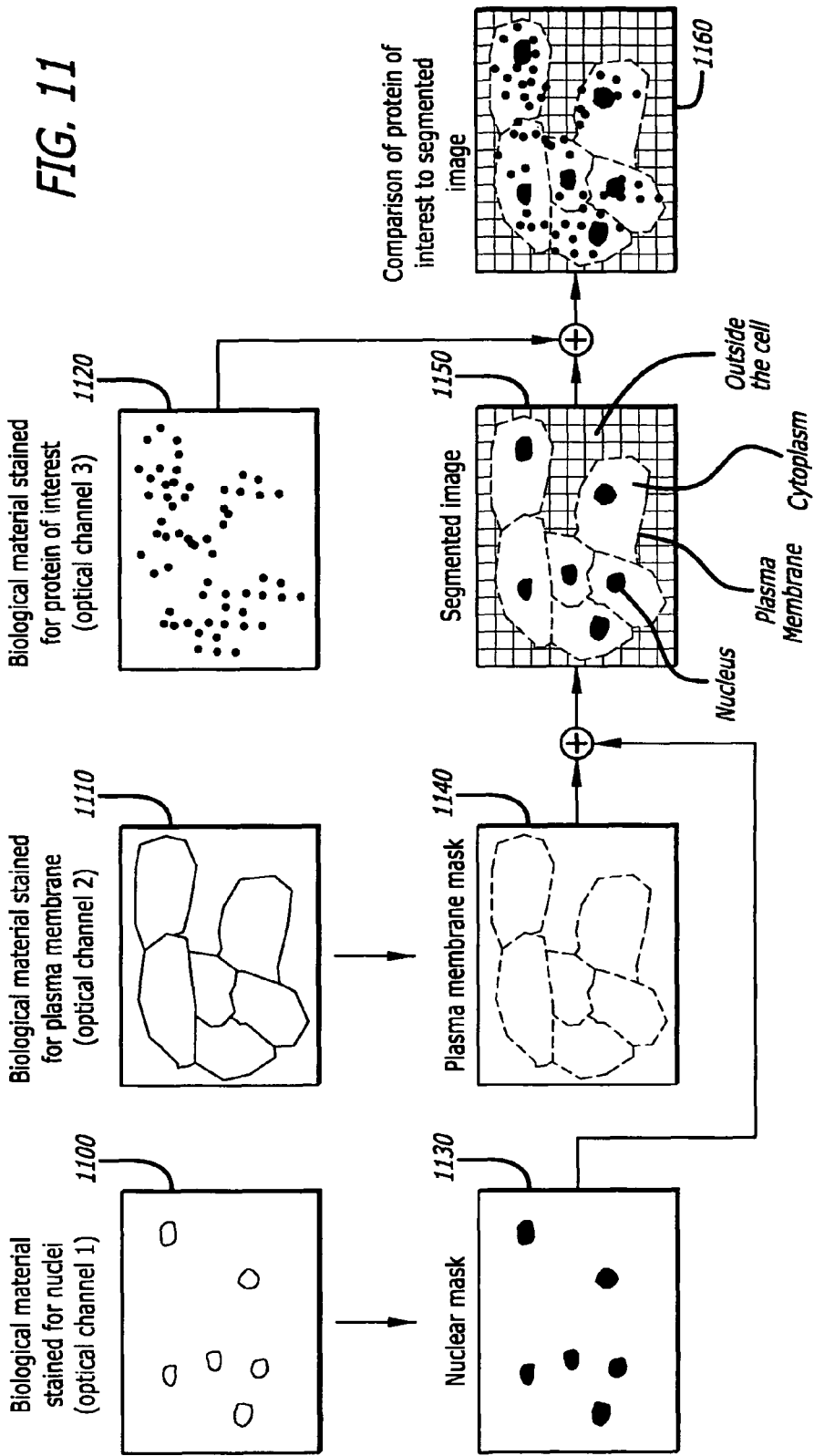
FIG. 11 is a flowchart representing steps combining images in more than two channels to obtain distribution of a protein of interest within cellular compartments.

It should be evident that the forgoing descriptions are not exhaustive of the uses to which the algorithms and kits may be put. For example, the same biological material can be imaged in multiple optical channels (each channel is characterized by a unique combination of excitation light and emitted light) to obtain multiple overlapping images of the same field of view. The different stains and optical channels may visualize different features in the image. Staining general features of the cells, such as the nuclei, or the plasma membrane, can be used to identify areas of the image as belonging to specific cellular regions. For example, staining the cells for the nuclei and for the plasma membrane allows every portion of the image to be classified as being either 1) at the plasma membrane (the portions of the image stained by the stain specific the plasma membrane), 2), in the nucleus (the portions of the image stained by the nuclear stained), 3), in the cytoplasm (the region of the cell between the nucleus and the plasma membrane), 4), outside the cell (in regions between two plasma membranes in which there are no nuclei). Thus, the image may be segmented by assignment of different portions of the image to specific and defined cellular regions. Information garnered by segmenting the image in this manner can be applied to information obtained with additional stains and optical channels. For example, with reference to FIG. 11, the biological material can be stained for nuclei (1100), for the plasma membrane (1110), and for a protein of interest (1120) (alternatively, the stain may visualize non-protein molecules of interest or cellular structures of interest) using at least three different stains to establish at least three separate optical channels. The staining patterns obtained with the nuclear and plasma membrane stains can be used to generate nuclear and membrane masks 1130 and 1140, and the nuclear and membrane masks may be combined to produce a segmented image 1150. The staining pattern 1120 obtained with the stain specific for the protein of interest can then be combined with the segmented image to produce an image 1160. Using the image 1160, the measurements in TABLE I may be made, and the distribution and concentration of the protein of interest in the image regions corresponding to the plasma membrane, nuclei, cytoplasm, and extracellular regions may be measured.

In this regard, consider the cadherin examples given above. Generally, cadherins comprise a protein family that is found at cell to cell junctions for virtually every cell type. There are approximately 80 different cadherin proteins in the human genome. While each cadherin is a unique sequence of amino acids over the entire length of the protein, the 24 amino acids of the carboxy-terminus are identical or nearly identical for all cadherin proteins. Antibodies directed against the carboxy terminus of N-cadherin (referred to as pan-cadherin antibodies) thus bind to the carboxy termini of all of the cadherin family members, even cadherins isolated from different species of animal (e.g., human, rat, mouse, etc.). Since cadherins span the cell membrane, this means that pan-cadherin antibodies (either polyclonal antibodies produced in rabbits, or monoclonal antibodies produced by murine-based hybridomas) can be used to visualize the location of the plasma membrane in biological material representing virtually all cell types. Pan-cadherin antibodies, can be visualized through use of secondary antibodies (such as goat-anti-rabbit, or goat-anti-mouse antibodies) conjugated to fluorophores (e.g., FITC, Cy2, Cy3, Texas Red) that will bind to the pan-cadherin antibody. Pan-cadherin antibodies can also be conjugated directly to fluorophores, resulting in a primary cadherin antibody that is fluorescent in which case a secondary antibody will not be required to visualize the cadherins within the biological material. In combination with a nuclear stain, such as DAPI, and the membrane activation algorithm described above, pan-cadherin antibodies can be used to segment an image of biological material into compartments corresponding to the plasma membrane, the cytoplasm, the nucleus, and regions of the image that are outside of the cells. A third optical channel can then be used, in combination with stains, to visualize a protein of interest (or a non-protein molecule or cell structure of interest). Referencing the image obtained with the protein of interest to the segmented image obtained with the pan-cadherin antibody and nuclear stain will allow the distribution of the protein within all of the aforementioned cellular compartments (nuclear, plasma membrane, and cytoplasm) to be defined.

A kit for visualization of cadherins may include a primary antibody against pan-cadherin (which may be a rabbit polyclonal antibody such as Panomics catalogue # E2364 or Abcam ab6529 or a mouse monoclonal antibody such as abcam ab6528) and a secondary antibody to the pan-cadherin antibody (such as a Texas-Red conjugated goat anti-mouse antibody (Jackson ImmunoResearch Laboratories, Inc 115-075-146) or a Texas-Red conjugated goat anti-rabbit antibody)). Preferably, the primary antibody would be used in an approximate 1/100 dilution (optimized on a lot-by-lot basis) in the blocking buffer and the secondary antibody would be used in an approximate 1/1500 dilution (optimized on a lot-by lot basis).

In a plurality of kits, pan-cadherin antibodies may be used to visualize the plasma membrane (in combination with the nuclear stain, providing a means of segmenting the cell images into nuclear, cytoplasmic, plasma membrane portions and portions of the images outside the cells). These kits may also include antibodies or stains against a protein of interest or against a non-protein molecule of interest (for example, but not limited to a carbohydrate or lipid), or to a cellular structure of interest (for example, but not limited to, a vesicle, caveolae, intercalated disk, myofibril, microtubule, intermediate fiber, or stress fiber). In cases where the target protein is detected by a primary antibody, a secondary antibody will also be used to detect the primary antibody. The fluorescence moiety attached to the secondary antibody (e.g., Texas Red, FITC, Cy2, or Cy3) will fluoresce in a different optical channel than the fluorescence moiety attached to the secondary antibody used to detect the pan-cadherin antibody. In all cases (detection of a protein of interest, a non-protein molecule of interest, or a cellular structure of interest), separate optical channels will be used to detect the nucleus, cadherins, and protein of interest (or non-protein molecule of interest, or structure of interest). Additionally, such kits may support additional optical channels (for example, but not limited to, a total of 4, 5, or 6 optical channels), allowing detection and quantification of multiple proteins of interest, non-proteins of interest, and/or cellular structures of interest.

Although the invention has been described with reference to the presently preferred embodiment, it should be understood that various modifications can be made without departing from the spirit of the invention. Accordingly, the invention is limited only by the following claims.

We claim:

1. A computerized method for analyzing an original magnified image of cells, comprising the high throughput microscopy system executed steps of:
    generating a first membrane mask by enhancing the traces of membrane outlines in cells in a normalized original image using at least a first enhancement function and then thresholding the enhanced traces of the membrane outlines;
    generating a first enhanced membrane image from the first membrane mask;
    generating a second membrane mask by enhancing the traces of membrane outlines in cells in the normalized original image using at least a second enhancement function and then thresholding the enhanced traces of the membrane outlines;
    generating a second enhanced membrane image from the second membrane mask;
    generating a composite enhanced membrane image by combining the first and second enhanced membrane images;
    generating markers associated with nuclei of the cells;
    generating a contour mask of membrane outlines with a contour finding function that applies the markers to the composite enhanced membrane image;
    generating an enhanced membrane mask from the contour mask; and,
    measuring structures of cellular components in the original image with the enhanced membrane mask.

2. The method of claim 1, wherein the contour finding function is a watershed algorithm.

3. The method of claim 2, wherein generating an enhanced membrane mask from the contour mask includes thickening lines of the contour mask.

4. The method of claim 1, wherein generating an enhanced membrane mask from the contour mask includes thickening lines of the contour mask.

* * * * *